United States Patent

Tsukada et al.

[11] 4,233,156
[45] Nov. 11, 1980

[54] LIQUID CHROMATOGRAPHY APPARATUS

[75] Inventors: Katsuo Tsukada, Nakamachi; Sadabumi Ohnuma, Hitachi, both of Japan

[73] Assignee: Hitachi, Ltd., Japan

[21] Appl. No.: 18,334

[22] Filed: Mar. 7, 1979

[30] Foreign Application Priority Data

Mar. 10, 1978 [JP] Japan .................. 53/26554

[51] Int. Cl.$^3$ ............................................. B01D 15/08
[52] U.S. Cl. ............................ 210/101; 73/61.1 C;
 210/198 C; 210/138
[58] Field of Search .............. 210/101, 198 C, 138;
 73/61.1 C

[56] References Cited

U.S. PATENT DOCUMENTS

| 3,917,531 | 11/1975 | Magnussen | 210/198 C |
| 4,045,343 | 8/1977 | Achenet et al. | 210/198 C |
| 4,128,476 | 12/1970 | Rock | 210/198 C |

*Primary Examiner*—John Adee
*Attorney, Agent, or Firm*—Craig and Antonelli

[57] ABSTRACT

A plurality of liquid mobile phases stored in a plurality of reservoirs respectively are filled and pumped by a dual pump driven by a stepping motor, through valves complementarily subjected to on-off control by a gradient programmer. The dual pump has two pistons in contact with the periphery of a cam in opposition to each other at 180 degrees, which pistons fill and pump the liquid mobile phases by linear reciprocation along the contour of the cam with the rotation of the cam. The radius of the cam linearly increases in the range from 0 to 180 degrees and linearly decreases in the range from 180 to 360 degrees at the same rate as when it increases. An electric signal is produced from a timing device during a period from the rotational positions of the cam reaches 0 and 180 degrees to a predetermined rotational positions. The liquid mobile phase delivered from the dual pump is supplied to a pressure transducer, and after passing through it, supplied to a column through an injector for injecting a specimen. The components into which the specimen is separated are detected by a detector. When the timing device detects that the cam is positioned in intervals from 0 and 180 degree to a predetermined angle therefrom, the motor control circuit drives the stepping motor at high speed during period from a time which the time derivative of the back pressure signal from the pressure transducer reaches value smaller than a predetermined value to a time it reaches value larger than the predetermined value.

12 Claims, 10 Drawing Figures

LIQUID CHROMATOGRAPHY APPARATUS

BACKGROUND OF THE INVENTION

1. Field of the Invention

The present invention relates to a liquid chromatography apparatus, or more in particular to a high pressure liquid chromatography apparatus comprising liquid-supply means adapted for supplying a liquid mobile phase to a column by means of a dual pump, i.e., two reciprocating piston pumps.

2. Description of the Prior Art

In a liquid chromatography apparatus comprising a dual pump for supplying a liquid mobile phase to the column, it is well known to produce the output flow of the pump, i.e., to accomplish the pumping operation without pulsation in order to carry out with high accuracy the quantitative analysis of the specimen components separated by the column.

An example of such an apparatus is disclosed in U.S. Pat. No. 3,917,531 entitled "Flow Rate Feedback Control Chromatograph". In the dual pump used in this patent, the production of the output flow of the pump, i.e., the pumping can be accomplished without pulsation, while the input flow of the pump, i.e., the filling thereof cannot be accomplished without pulsation. Therefore, in the case where two liquid mobile phases are programmably mixed by the method controlling opening time of two valves which are put on the suction side of the pump, the liquid mobile phase mixture ratio cannot be exactly proportioned to the opening time of the valves.

In FIG. 1 showing the flow pattern of the two pistons of the dual pump, pistons Nos. 1 and 2 of the above-mentioned U.S. Patent, the abscissa represents time and the ordinate the time derivative of displacement of the pistons dx/dt, where X shows the displacement of the pistons. Let the maximum value of dx/dt at the time of pumping of pistons Nos. 1 and 2 be j, and the value dx/dt during the overlap of the pumping operation of pistons Nos. 1 and 2 be l and k respectively. As seen from the graph, relation $k+l=j$ is established during the pumping overlap. According to the dual pump disclosed in the cited U.S. Patent, therefore, the output flow of the dual pump, that is, the pumping operation is accomplished without pulsation. During the input flow, i.e., the filling operation of the dual pump, however, both pistons Nos. 1 and 2 fail to fill at the portion designated as n in the drawing. The presence of this portion n disables the filling operation without pulsation in the cited U.S. Patent.

As a result, the liquid chromatography apparatus disclosed in U.S. Patent has a disadvantage in the suction of liquid mobile phase as mentioned above.

SUMMARY OF THE INVENTION

An object of the present invention is to provide a liquid chromatography apparatus capable of both filling and pumping the liquid mobile phase without pulsation in supplying the same by the dual pump.

Another object of the present invention is to provide a high-pressure liquid chromatography apparatus capable of both filling and pumping the liquid mobile phase without pulsation in supplying the liquid mobile phase by the dual pump.

Still another object of the present invention is to provide a reliable high-pressure liquid chromatography apparatus capable of both filling and pumping the liquid mobile phase in supplying the liquid mobile phase by the dual pump.

A further object of the present invention is to provide a high pressure liquid chromatography apparatus with a simple control system for filling and pumping the liquid mobile phase without pulsation in supplying the liquid mobile phase by the dual pump.

According to the present invention, there is provided a liquid chromatography apparatus comprising a cam for reciprocating the pistons of the dual pump, which cam is so shaped that, during the rotation thereof at a fixed speed, the time derivative of displacement for the pistons dx/dt increases or decreases always linearly. As a result, the displacement of the pistons for unit time of filling and pumping operations is kept constant, thus making possible the filling and pumping of the liquid mobile phase without any pulsation.

DESCRIPTION OF THE PREFERRED EMBODIMENTS

Figure 1:
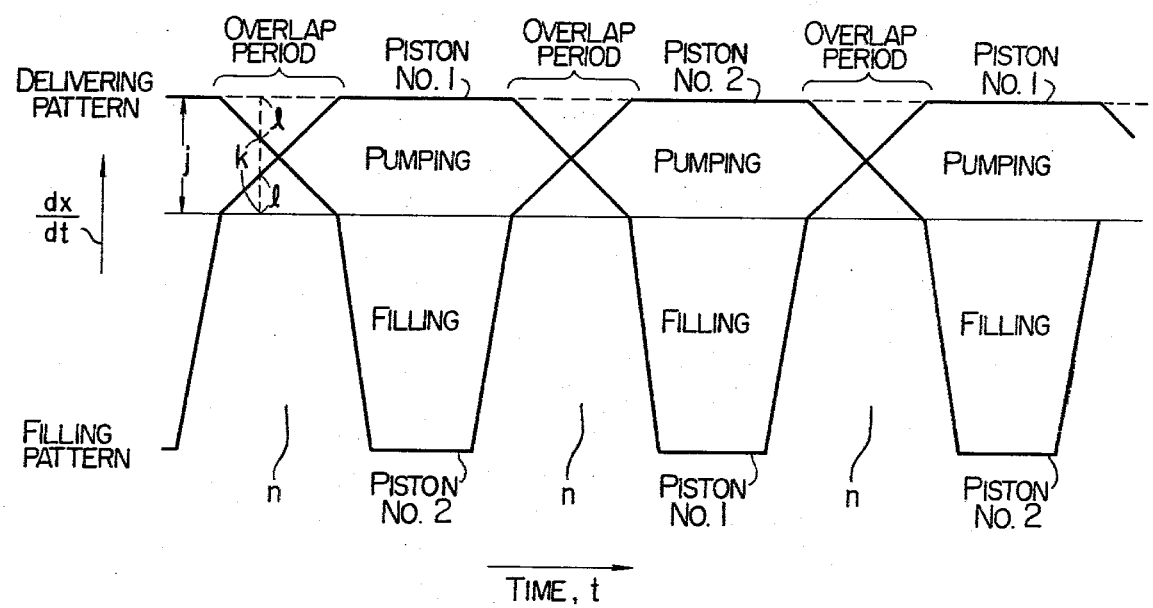
FIG. 1 is a diagram showing a flow pattern of a conventional dual pump.
Figure 2:
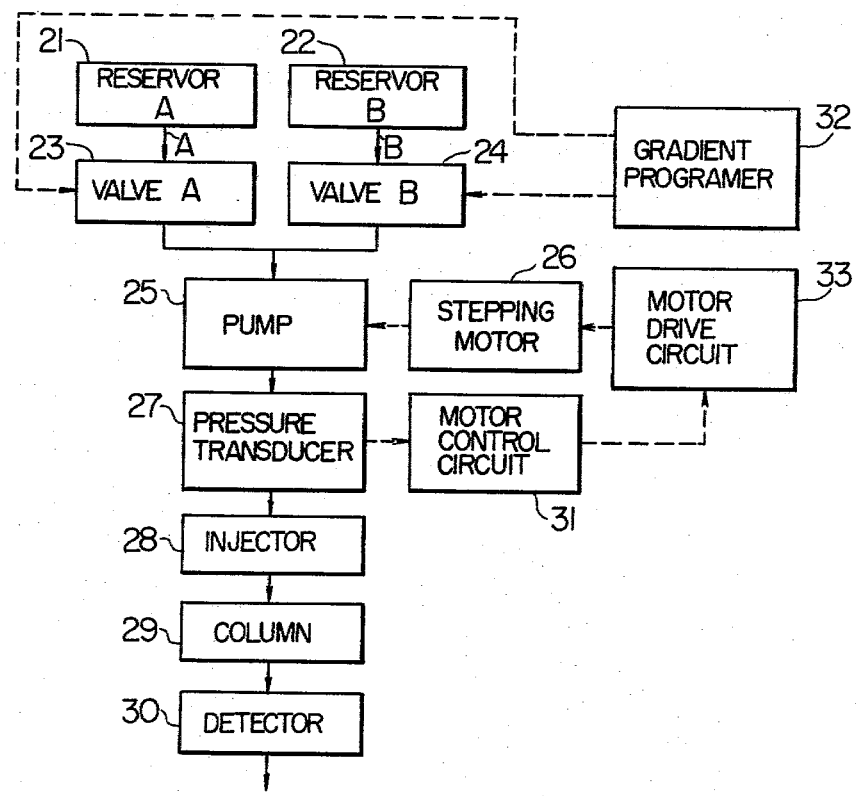
FIG. 2 is a simplified block diagram setting forth the basic elements, including the electrical control elements, of a chromatography system in accordance with the present invention.

A simplified block diagram of the liquid chromatography apparatus according to the present invention is shown in FIG. 2.

Figure 3:
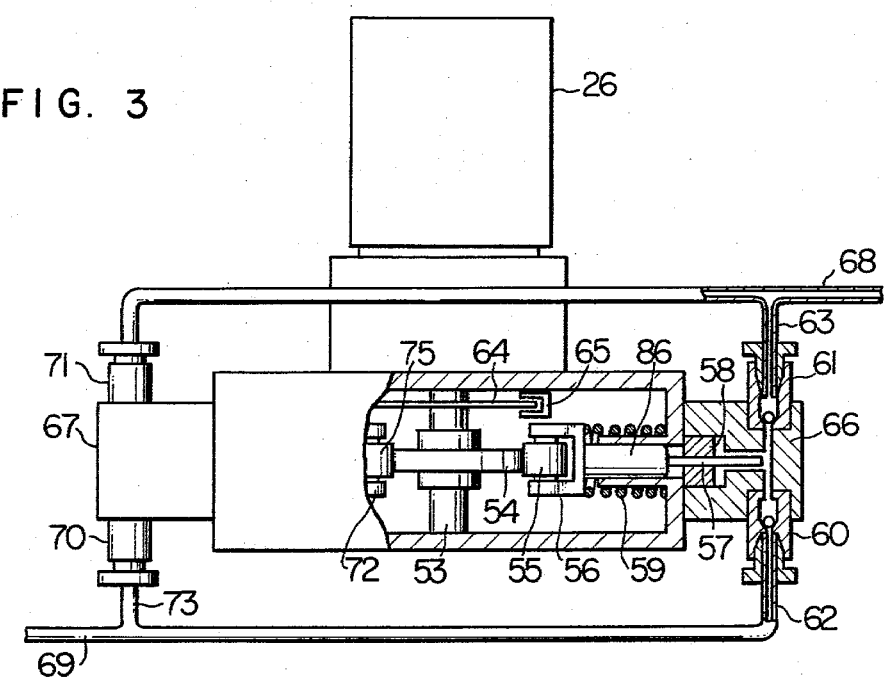
FIG. 3 is a partly cut-away side view showing a dual pump used with the apparatus according to the present invention.

The liquid mobile phase is stored in the reservoirs A and B designated by numerals 21 and 22 respectively. The liquid mobile phase in the reservoirs A and B are filled in the dual pump 25 through valves A and B designated by 23 and 24 respectively. As shown in FIG. 3, the pump 25 is a small-capacity dual pump of a reciprocating piston type, the output flow rate of which is controlled by changing the reciprocating velocity of the pistons. The liquid mobile phase pumped out of the pump 25 is supplied to the column 29 through the pressure transducer 27 and the injector 28. The pressure transducer 27 is for producing an electrical signal proportional to the flow rate. The injector 28 is for injecting a specimen into the liquid mobile phase. The column 29 is for separating the specimen injected into the injector 28 into components. The detector 30 is for detecting the specimen components separated by the column 29.

As will be described later, the dual pump 25 fills and pumps out the liquid mobile phase always at a fixed flow rate. In other words, it accomplishes filling and pumping operations without any pulsation. In view of the feature that the liquid mobile phase continues to be filled at a fixed rate, the dual pump according to the present invention is capable of supplying the column with the liquid mobile phase of a desired mixing ratio at high accuracy without any restrictions on the suction of the liquid mobile phase.

The valves A and B are complementary with each other so that they operate in such a manner that when valve A is open, the valve B is closed. That is, when one of the valves is open, the other valve is closed without fail. The dual pump 25 continues to suck the liquid mobile phase always at a fixed flow rate, and therefore the liquid mobile phase A or B in reservoir A or B in the amount exactly proportional to the time during which the valve A or B respectively is open is filled in the dual pump 25. For this reason, by alternately opening and closing the valves A and B and controlling the open time of the respective valves, a mixture liquid of liquid mobile phases A and B of a desired mixing ratio is supplied to the column 29. Further, it is possible to change the mixing ratio with time. The timing of alternative opening and closing of the valves A and B is controlled by the gradient programmer 32. The pump 25 is driven by the stepping motor 26, which in turn is rotated by the output of the motor drive circuit 33. The motor control circuit 31 operates in such a manner as to eliminate an undesirable flow rate variation in response to the output from the pressure transducer 27, i.e., the feedback signals.

In the case where the supply system for the liquid mobile phase of the present invention is embodied in what is called a low-pressure liquid chromatography apparatus 100 kg/cm$^2$ or lower, the pressure transduce 27 and the motor control circuit 31 are not necessarily required.

Figure 4:
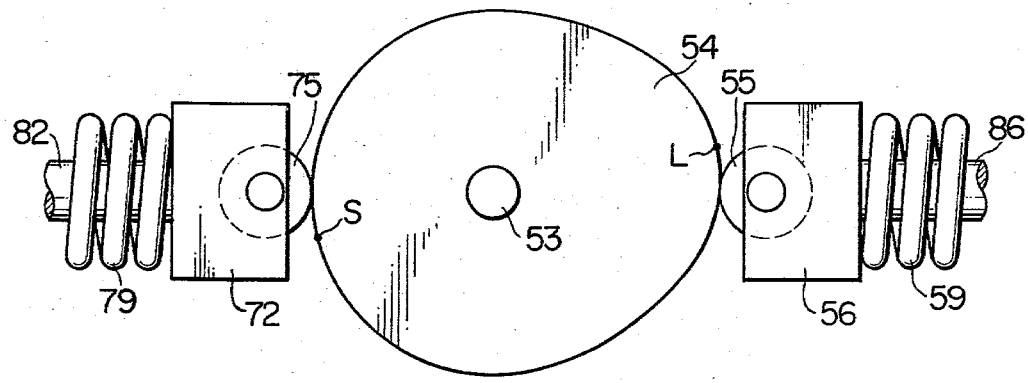
FIG. 4 is an enlarged front view showing the cam and part of the pistons shown in FIG. 3.

The general configuration of the dual pump 25 used in the present invention will be explained below with reference to the partially cut-away side view of FIG. 3. FIG. 4 is an enlarged front view including the cam and part of the pistons of FIG. 3.

A pair of pistons 86 and 82 which are positioned 180 degrees apart from each other are opposed to the cam 54. The dual pump 25 includes liquid supply sections 66 and 67. The plunger 57 sealed hermetically by the seal 58 reciprocates laterally. Take the liquid supply section 66 as an example. When the plunger 57 moves leftward, the suction-side check valve 60 is closed and the discharge-side check valve 61 opens, so that the liquid mobile phase is discharged via the discharge tube 63. The plunger 57 is fixed on the plunger holder 56, which in turn is kept in contact with the cam 54 through the bearing 55 by the force of the spring 59. Thus the plunger 57 reciprocates exactly following the profile of the cam 54. The cam 54 is rotationally driven by the stepping motor 56 through the shaft 53.

Figure 5:
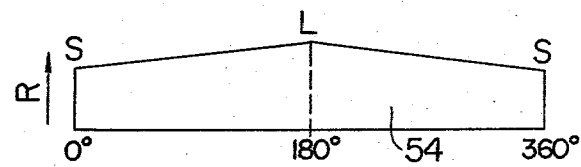
FIG. 5 is a diagram for explaining the geometry of the cam shown in FIG. 6, where the abscissa represents the angle, and the ordinate the radius from the cam center to the cam periphery.

FIG. 5 is a diagram where the abscissa represents the angle and the ordinate the radius R from the cam center to the cam periphery for explaining the geometry of the cam. The radius R is minimum at the angle of 0, i.e., 360 degrees, and maximum at 180 degrees. The point S on the periphery of the cam 54 in FIG. 4 corresponds to the point S on the outer periphery of the cam at the cam angle of 0 or 360 degrees in FIG. 5; while the point L represents the point L on the outer periphery of the cam at cam angle of 180 degrees in FIG. 5. As seen from FIG. 5, the radius R of the cam 54 increases linearly from 0 to 180 degrees and is reduced linearly from 180 to 360 degrees at exactly the same rate as in the increase.

Figure 6:
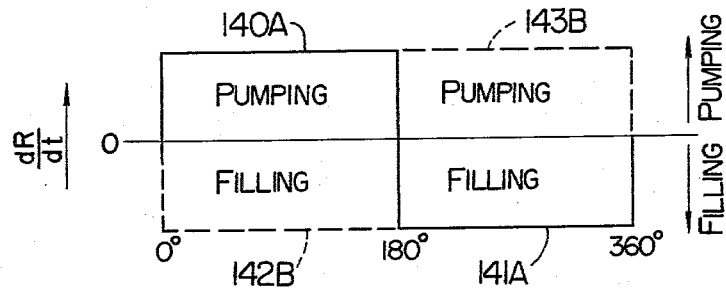
FIG. 6 is a diagram showing a flow pattern of the dual pump according to the present invention when the cam is rotating steadily at a low back pressure in the column.

Assuming that the cam 54 is rotated at a fixed velocity, the plunger 57 and hence the piston 86 moves at the speed of dR/dt as shown in FIG. 6. In other words, the piston alternates between pumping and filling operations at a fixed speed at intervals of 180 degrees. The cam 54 has a shape symmetrical with respect to the straight line connecting the points S and L thereon. Therefore, if the plunger 57 of the liquid supply section 66 is driven along the solid line in FIG. 6, for example, the plunger of the liquid supply section 67 reciprocates in the manner shown by the dashed line. In FIG. 6, reference numeral 140A shows the output flow rate of the liquid supply section 66, and numeral 141A the suction flow rate of the liquid supply section 66. Numeral 142B shows the suction flow rate of the liquid supply section 67, and numeral 143B the output flow rate of the liquid supply section 67. The liquids from the liquid supply sections 66 and 67 are synthesized so that the liquid mobile phase is discharged from the outlet 68 of FIG. 3, toward the column at fixed flow rate without any pulsation, and the liquid mobile phase is taken into the inlet 69 at fixed flow rate without any pulsation. Numeral 70 shows a suction side check valve for the liquid supply section 67, numeral 71 an output-side check valve, and numeral 73 a suction tube.

In the case where the system shown in FIG. 2 is used in the high pressure liquid chromatography apparatus, it is required to consider the degree of compression of the liquid mobile phase.

That is to say, when the back pressure in the column is high, the pumping operation is started only after the liquid pressure in the liquid supply section 66 or 67 of FIG. 3 becomes equal to the back pressure of the column. As to the filling process, on the other hand, it is not started until the liquid pressure in the liquid supply section 66 or 67 returns to the normal level.

Figure 7:
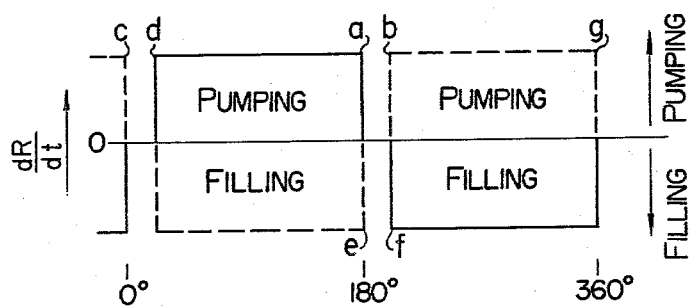
FIG. 7 is a diagram showing a flow pattern of the dual pump according to the present invention when the cam is rotating steadily at a high back pressure in the column.

Therefore, in the case where the back pressure in the column is high, both the pumping and filling operations are accompanied by pulsation as shown in FIG. 7. In this case, the coverage of the pistons 86 and 82 required to compress the liquid from normal level to the back pressure level is exactly equal to the coverage of the pistons 86 and 82 required for reducing the back pressure to normal pressure level. For this reason, the pulsation width a-b for the pumping operation is equal to the pulsation width e-f for the filling operation as shown in FIG. 7. In view of this, the present invention employs a method in which the cam 54 is rotated at higher speed during the sections a-b and c-d to instantaneously end the periods a-b and c-d in order to obviate the problem of the pulsating flow. The cam 54 is of course rotated at a predetermined speed during the sections b-g and d-a. In other words, the cam 54 is rotated at higher speed than the predetermined speed only for a certain angle from the cam position of 0 and 180 degrees.

The cam positions of 0 and 180 degrees are detected by the combination the chopper rotating about the same axis as the cam 54 and the position detector 65 as shown in FIG. 3. The combination of the chopper 64 and position detector 65 is a well-known prior art method widely used with such apparatuses as the photometer. The starting point of the high-speed rotation can be detected by the above-mentioned method, while the final point of high-speed rotation, i.e., the positions b and d in FIG. 7 cannot be detected in a similar manner. This is because the positions b and d depend on the back pressure of the column.

The positions b and d are detected by use of the signal from the pressure transducer 27 shown in FIG. 2. The pressure transducer 27 is for converting pressure into an electrical signal and uses such a device as a strain gauge. When the back pressure of the column reaches the position b or d in FIG. 7, the pressure detected by the pressure transducer 27 suddenly increases. The point up to which the output of the pressure transducer 27 has increased corresponds to the positions b and d in FIG. 7. Thus the sections a-b and c-d in FIG. 3 are detected in the form of electrical signal, so that this electrical signal is fed back to the motor control circuit 31 of FIG. 2, thereby achieving high-speed rotation during the sections a-b and c-d. For such a control of the rotational speed, a stepping motor which rotates at a speed proportional to the number of input pulses is suitable and convenient for embodying the present invention.

Figure 8:
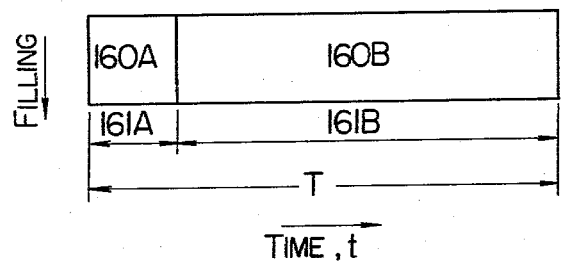
FIG. 8 is a time chart showing a cycle of operation of the valves for producing a mixture liquid when a gradient is involved.

In this way, a dual pump is obtained, which is capable of filling and pumping always at a fixed flow rate without pulsation regardless of the magnitude of the back pressure of the column. Thus, as shown in FIG. 8, the liquid mobile phases A and B of a capacity proportional to the open time of valves A and B are filled and pumped by the dual pump 25 and supplied to the column 29. In other words, only by accurately regulating the operating time of the valves A and B, the liquid mobile phase of a desired mixing ratio is supplied to the column 29 with high accuracy regardless of the magnitude of the back pressure of the column 29. In FIG. 8, reference character T shows one cycle of valve operation, numeral 161A the open time of valve A, numeral 161B the open time of valve B, numeral 160A the filling capacity of the liquid mobile phase A, and numeral 160B the filling capacity of the liquid mobile phase B. Preferably, a solenoid valve or the like is used as valves A and B. In this case, due to the limitation of the response speed of the valves, the open time of valves A and B cannot be reduced infinitely. In order to obtain a mixing ratio in which the proportion of one of the liquid mobile phases is extremely small as compared with that of the other liquid mobile phase, the time T of one operating cycle of the valves is required to be lengthened. According to the present invention, a desired length of one operating cycle T may be determined in accordance with the required minimum mixing ratio for the reason that the dual pump 25 is always capable of filling operation without pulsation at a fixed flow rate. Further, in view of the fact that the time length T of one operating cycle may be set as desired, three or more valves may be provided for producing a mixture liquid containing three or more different liquid mobile phases with high accuracy. Incidentally, the points a and c in FIG. 7 may be detected by detecting the reduction in back pressure of column 29 through the pressure transducer 27, and therefore the position detectors 64 and 65 for the cam 54 in FIG. 3 may be done without.

The electric signals from the position detector 64 and 65 and the pressure transducer may be ANDed in order to prevent the motor drive circuit 33 from responding to a noise from the pressure transducer 27 whereby the pump control is exactly achieved. When the range of cam position in which the cam can be rotated with high speed is predetermined, the points b and d in FIG. 7 are detected without being affected by a noise. In order to achieve this, the position detectors 64 and 65 generate output signal having high level during a predetermined period from the angle positions 0 to 180 degrees of the cam 54 to an angle position fully covering the sections a-b and c-d. The pressure transducer 27 is adapted to detect the fall and rise points of the back pressure during the high level output of the position detectors 64 and 65 and to generate high level signal during the period from the fall point to the rise point. Accordingly, an AND signal between the signal from the position detectors 64 and 65 and the signal from the pressure transducer determines an accurate period to be rotated with high speed, as a result, the system is controlled under high reliability.

Figure 9:
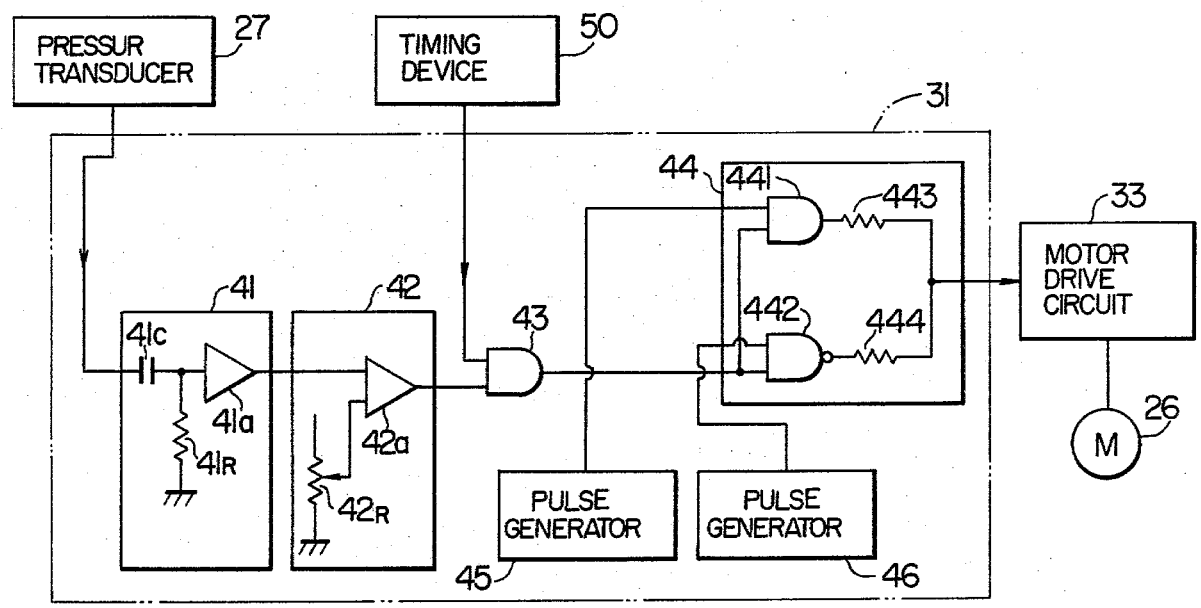
FIG. 9 is a detailed block diagram of the motor control circuit of FIG. 2.

An embodiment of the motor control circuit 31 in FIG. 2 is shown in FIG. 9. The output signal from the pressure transducer 27 is differentiated by the differentiator 41. Numeral 41C shows a capacitor, numeral 41R a resistor, and numeral 41a an amplifier. The output of the differentiator 41 is applied to the comparator 42, which produces a high level output when the output of the differentiator 41 is reduced below the output level predetermined by the resistor 42R which is a negative value near zero so as to prevent the effect of a noise. A logic product of the output of the comparator 42 and the output of the timing device 50 including the cam position detectors 64 and 65 of FIG. 3 is taken by the AND circuit 43, which produces an output when both the outputs are "high". The output of the AND circuit 43 is applied to the switching circuit 44. The high frequency pulse generaor 45 is for driving the stepping motor 26 at high speed when the output of the AND circuit 43 is high level. The variable frequency pulse generator 46 is for driving the stepping motor 26' at steady speed when the time derivative of the pressure detected by the pressure transducer 27 reaches a level larger than the predetermined value by sharp rising thereof.

The switching circuit 44 includes an AND circuit 441 and a resistor 443. The AND circuit 441 is impressed with output from the AND circuit 43 and the output from the high frequency pulse generator 45. The output of the switching circuit 44 is produced to the motor drive circuit 33 through the AND circuit 441 and the resistor 443 to drive the stepping motor 26 at high speed. On the other hand, the output of the variable pulse generator 46 and the low-level output of the AND circuit 43 are applied to the NAND gate 442 which produces to the motor drive circuit 33 an output for driving the stepping motor 26 at normal speed through the resistor 444.

Figure 10:
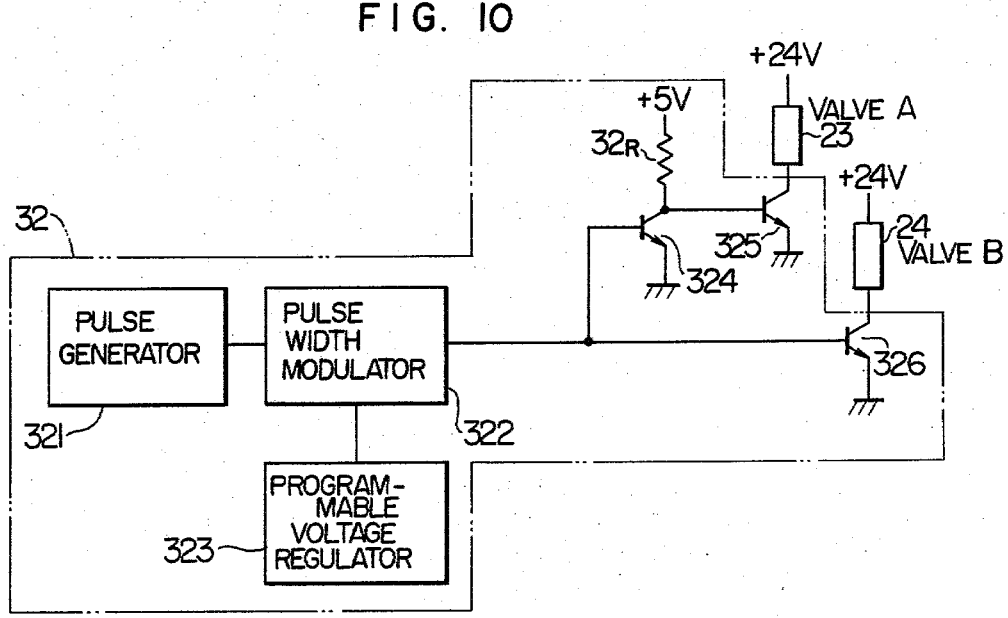
FIG. 10 is a block diagram showing a gradient programmer for complementary on-off control of the valves shown in FIG. 2.

A circuit configuration of the gradient programmer 32 of FIG. 2 is shown in FIG. 10. The pulse generator 321 is for producing a pulse of a period equivalent to the time required for the valves A and B to open and close once respectively. The programmable voltage regulator 323 is for changing the voltage level of the pulse width modulator 322 in the range from 0% to 100% and may comprise, for example, the voltage regulator disclosed in U.S. Pat. No. 3,398,689 entitled "Apparatus Providing a Constant-Rate Two-Component Flow Stream". The pulse width modulator 322 is for modulating the width of the pulse generated from the pulse generator 321 in response to the output of the programmable voltage regulator 323. This pulse width modulator 322 may comprise, for example, NE555 Linear IC made by Intersil Inc.

In response to the output of the pulse width modulator 322, the transistor 326 control the operation of the valve B. The valve A is subjected to on-off operation complementary to that of valve B by the transistors 324 and 325. The gradient programmer 32 is not required to control the operating timing of the valves A and B in response to the input signals from the motor control circuit 31 as described above, thus symplifying the circuit configuration.

We claim:

1. A liquid chromatography apparatus comprising:
   at least one reservoir for storing at least one liquid mobile phase;
   at least one valve for controlling the liquid mobile phase flowing out of said at least one reservoir;
   a reciprocating dual-piston pump including two pistons for filling two chambers with the liquid mobile phase flowing out of said valve and pumping alternately the liquid mobile phase filled in said chambers, one end of each piston being in contact with the periphery of a rotatable cam in opposition to one end of the other piston at 180 degrees, the other end of each piston extending into each of said chambers, each of said pistons being reciprocated linearly along the contour of said cam with the rotation of said cam, thus filling said liquid mobile phase into said chambers and pumping said liquid mobile phase out of said chambers;
   an injector for injecting a specimen into the liquid mobile phase passed through said pump;
   a column for separating the specimen injected by said injector, into components;
   a detector for detecting the components of said specimen separated by said column;
   a programmer for controlling the operating time of said at least one valve;
   motor means coupled to said cam of said pump for driving said pump through successive cycles of reciprocation;
   said cam having a shape such that when the time derivative of displacement of one piston is positive over an angle range, the time derivative of displacement of the other piston is a negative fixed value over substantially the entire angle range that said one piston is positive, and when the time derivative of displacement of said one piston is negative over an angle range, the time derivative of displacement of said other piston is a positive fixed value over substantially the entire angle range that said one piston is negative.

2. A liquid chromatography apparatus according to claim 1, further comprising:
   a pressure transducer connected between said reciprocating dual-piston pump and said injector for providing an electric signal proportional to the flow rate of said liquid mobile phase from said pump, and
   a motor control circuit for applying to said motor means a control signal for controlling the reciprocating speed of said reciprocating dual pistons in esponse to an electric signal from said pressure transducer.

3. A liquid chromatography apparatus according to claim 2, wherein said motor control circuit includes a circuit for providing a high-speed rotation command to said motor means until the time derivative of the electric signal provided from said pressure transducer reaches a level larger than a predetermined value.

4. A liquid chromatography apparatus according to claim 1, wherein said motor comprises a stepping motor, and
   said motor control circuit includes:
   a differentiator for differentiating an electric signal from said pressure transducer;
   a comparator which produces an output only when the output of said differentiator is reduced below a predetermined output value,
   a first AND circuit for calculating a logic product of the outputs of said timing device and said comparator and producing an output when both of said outputs are "high";
   a high frequency pulse generator for producing a high frequency pulse for driving said stepping motor at high speed when the output of said first AND circuit is high level;
   a variable frequency pulse generator for producing a variable frequency pulse for driving said stepping motor at a steady speed to correspond a predetermined discharge flow rate; and
   a switching circuit including
   an AND circuit impressed with the output of said first AND circuit and the output of said high frequency pulse generator, and producing to said motor drive circuit an output for driving said stepping motor at high speed when both of the outputs of said first AND circuit and said high frequency pulse generator are "high", and a NAND circuit impressed with the output of said first AND circuit and the output of said variable frequency pulse generator, and applying to said motor drive circuit an output for driving said stepping motor at steady speed in response to the output pulse of said variable frequency pulse generator when the output of said first AND circuit is "low".

5. A liquid chromatography apparatus according to claim 1, 2, 3, or 4 wherein said programmer includes a pulse generator for generating a pulse having an interval equivalent to the time required for at least one valve to operate once, a programmable voltage generator for changing the voltage value in the range from 0 to 100%, a pulse width modulator for changing the pulse width of the pulse generated from said pulse generator in the range from 0 to 100% in response to the output of said programmable voltage regulator, valve operating means for controlling the operation of at least one valve in response to the output of said pulse width modulator.

6. A liquid chromatography apparatus according to claim 1, 2, 3, 4 or 5, further comprising a plurality of valves for controlling each of said liquid mobile phases flowing out of said plurality of said reservoirs, said valve operating means including a circuit for controlling the operation of said plurality of said valves complementarily with each other in response to the output of said pulse width modulator.

7. A liquid chromatography apparatus according to claim 5, further comprising a plurality of valves for controlling each of said liquid mobile phases flowing out of said plurality of said reservoirs, said valve operating means including a circuit for controlling the operation of said plurality of said valves complementarily with each other in response to the output of said pulse width modulator.

8. A liquid chromatography apparatus according to claim 3, wherein said circuit for providing a high-speed rotation command comprises means for sending said command to said motor means when said pressure transducer detects a reduction in back pressure in said column.

9. A liquid chromatography apparatus according to claim 1, wherein said cam has a shape such that its radius increases linearly from 0 to 180 degrees and decreases linearly from 180 to 360 degrees, with the rate of increase of the radius being the same, in absolute value, as the rate of decrease of the radius.

10. A liquid chromatography apparatus comprising:
at least one reservoir for storing at least one liquid mobile phase;
at least one valve for controlling the liquid mobile phase flowing out of said at least one reservoir;
a reciprocating dual-piston pump including two pistons for filling two chambers with the liquid mobile phase flowing out of said valve and pumping alternately the liquid mobile phase filled in said chambers, one end of each piston being in contact with the periphery of a rotatable cam in opposition to one end of the other piston at 180 degrees, the other end of each piston extending into each of said chambers, each of said pistons being reciprocated linearly along the contour of said cam with the rotation of said cam, thus filling said liquid mobile phase into said chambers and pumping said liquid mobile phase out of said chambers;
an injector for injecting a specimen into the liquid mobile phase passed through said pump;
a column for separating the specimen injected by said injector, into components;
a detector for detecting the components of said specimen separated by said column;
a programmer for controlling the operating time of said at least one valve;
motor means coupled to said cam of said pump for driving said pump through successive cycles of reciprocation;
a pressure transducer connected between said reciprocating dual-piston pump and said injector for providing an electric signal proportional to the flow rate of said liquid mobile phase from said pump;
a motor control circuit for applying to said motor means a control signal for controlling the reciprocating speed of said reciprocating dual pistons in response to an electric signal from said pressure transducer, said motor control circuit including a circuit for providing a high-speed rotation command to said motor means until the time derivative of the electric signal provided from the pressure transducer reaches a level larger than a predetermined value; and
a timing device for applying an electric signal to said motor control circuit during a period from the cam rotational positions of 0 and 180 degrees to predetermined cam rotational positions, said motor control circuit including a circuit for issuing a high-speed rotation command to said motor means in response to an electric signal from said timing device until the time derivative of the electric signal produced from said pressure transducer reaches a value larger than a predetermined value;
said cam having a shape such that its radius increases linearly from 0 to 180 degrees and decreases linearly from 180 to 360 degrees, with the rate of increase of the radius being the same, in absolute value, as the rate of decrease of the radius.

11. A liquid chromatography apparatus according to claim 10, wherein said timing circuit includes a chopper adapted to rotate about the same axis as the cam and position detector means working in combination with said chopper to detect the cam positions of 0 and 180 degrees.

12. A liquid chromatography apparatus comprising:
at least one reservoir for storing at least one liquid mobile phase;
at least one valve for controlling the liquid mobile phase flowing out of said at least one reservoir;
a reciprocating dual-piston pump including two pistons for filling two chambers with the liquid mobile phase flowing out of said valve and pumping alternately the liquid mobile phase filled in said chambers, one end of each piston being in contact with the periphery of a rotatable cam in opposition to one end of the other piston at 180 degrees, the other end of each piston extending into each of said chambers, each of said pistons being reciprocated linearly along the contour of said cam with the rotation of said cam, thus filling said liquid mobile phase into said chambers and pumping said liquid mobile phase out of said chambers;
an injector for injecting a specimen into the liquid mobile phase passed through said pump;
a column for separating the specimen injected by said injector, into components;
a detector for detecting the components of said specimen separated by said column;
a programmer for controlling the operating time of said at least one valve; and
motor means coupled to said cam of said pump for driving said pump through successive cycles of reciprocation,
said cam having a shape such that its radius increases linearly from 0 to 180 degrees and decreases linearly from 180 to 360 degrees, with the rate of increase of the radius being the same, in absolute value, as the rate of decrease of the radius.

* * * * *